United States Patent [19]
Ries et al.

[11] Patent Number: 5,324,291
[45] Date of Patent: Jun. 28, 1994

[54] BONE SECTION REATTACHMENT APPARATUS AND METHOD

[75] Inventors: Michael Ries, Cooperstown, N.Y.; Carlos E. Gil, Bartlett; Steven A. Garner, Memphis, both of Tenn.

[73] Assignee: Smith & Nephew Richards, Inc., Memphis, Tenn.

[21] Appl. No.: 994,320

[22] Filed: Dec. 21, 1992

[51] Int. Cl.⁵ .............................................. A61B 17/58
[52] U.S. Cl. .................................... 606/71; 606/60; 606/69; 606/72; 606/74
[58] Field of Search .................. 606/53, 60, 61, 74, 606/69–72, 86, 87, 89, 103, 151; 128/898

[56] References Cited

U.S. PATENT DOCUMENTS

| | | | |
|---|---|---|---|
| 3,654,668 | 4/1972 | Appleton | 606/74 |
| 4,153,953 | 5/1979 | Grobbelaar | 606/64 |
| 4,269,180 | 5/1981 | Dall et al. | 606/69 |
| 4,889,110 | 12/1989 | Galline et al. | 606/69 |
| 4,960,420 | 10/1990 | Goble et al. | 606/72 |
| 4,988,351 | 1/1991 | Paulos et al. | 606/72 |
| 5,147,360 | 9/1992 | Dubousset | 606/72 |
| 5,190,545 | 3/1993 | Corsi et al. | 606/72 |
| 5,217,497 | 6/1993 | Mehdian | 606/69 |

FOREIGN PATENT DOCUMENTS 441668  8/1991  European Pat. Off. .............. 606/86

Primary Examiner—Stephen C. Pellegrino
Assistant Examiner—J. A. Schmidt
Attorney, Agent, or Firm—Pravel, Hewitt, Kimball & Krieger

[57] ABSTRACT

An implant for use in reattaching a bone section following bone surgery which includes a plate-like member for fitting over at least a portion of the outer surface of the bone section to be reattached. The plate has an inner surface for engaging the bone section and an outer surface facing away from the bone section and side walls extending between the inner and outer surface. The outer surface includes at least one cable holding portion for holding a cable in place. A rectangular body receives the ends of a cable and allows for gripping and holding the cable under tension. The rectangular body has opposing concave sides and a pair of openings parallel to the concave sides for receiving the end of the cable. The rectangular body is collapsible by a crimping tool which pinches the cable in the openings. A recess extends across the outer surface of the plate-like member for receiving the rectangular body with the recess intersecting the cable holding portions.

27 Claims, 4 Drawing Sheets

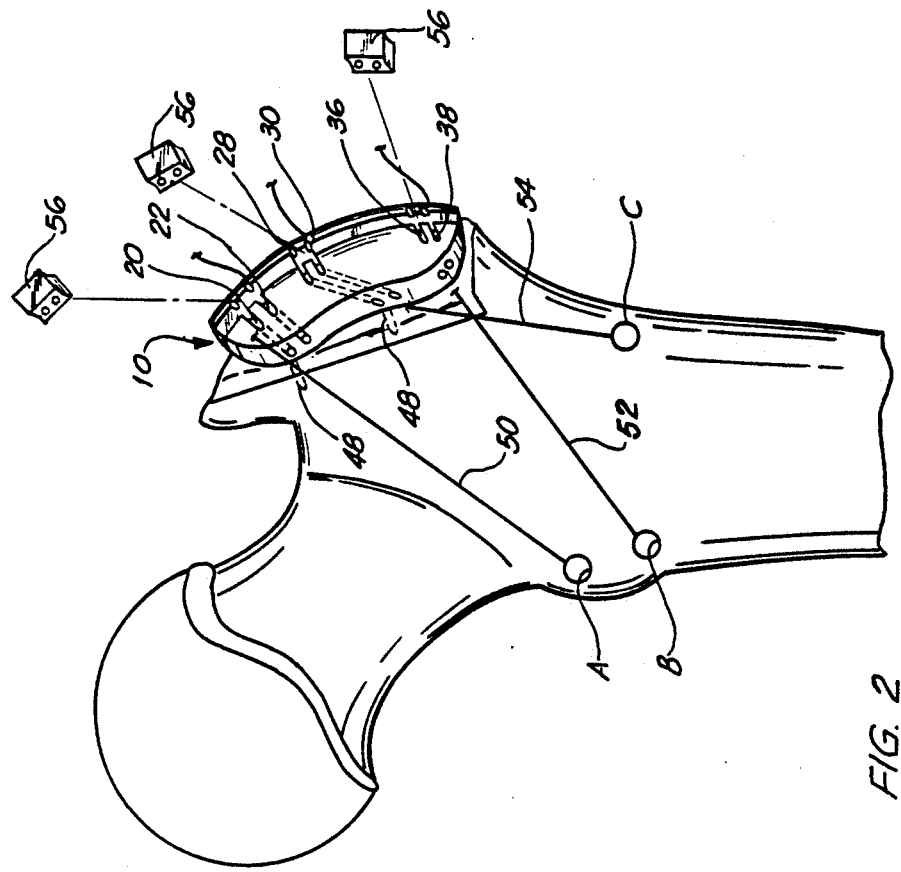
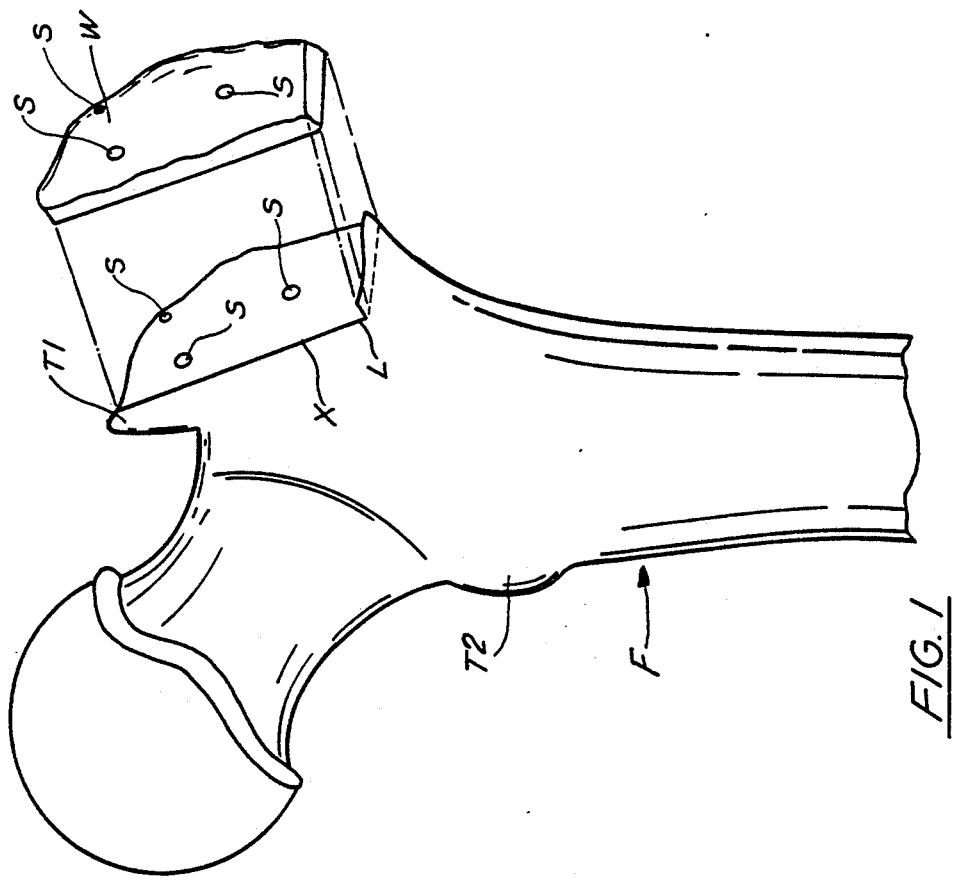

BONE SECTION REATTACHMENT APPARATUS AND METHOD

BACKGROUND OF THE INVENTION

1. Field of the Invention

The invention generally relates to an apparatus and method useful for the reattachment of a bone section removed during surgery and, more particularly, to a clamp and cable system for reattaching the dome portion of the greater trochanter to prevent migration of the removed bone section until it fuses to the remaining bone.

2. Description of the Related Art

Hip surgery often requires osteotomy of the dome portion of the greater trochanter to access the joint. Following such surgery it is important that the removed portion be clamped in place to promote efficient healing through fusion of the removed portion to the remainder of the femur.

Many surgeons simply reattach the removed trochanter section after implanting a hip prosthesis by wiring the section to the remainder of the trochanter. This has proved unsatisfactory because of forces that cause the section to shift or rotate when the patient is walking or raising from a seat. It is not uncommon for surgical wires to break because of the magnitude of such forces.

A trochanter reattachment system used in the past is known as the Dall-Miles system, described in U.S. Pat. No. 4,269,180. This system utilizes an H-shaped clamp which is held in place on the reattached bone section by teeth that engage the outer surface of the domed segment and others that are embedded. Cables are passed through holes in the bridge of the clamp and through holes drilled in the femur. The bridge of the clamp is crimped onto the cables to fix them in position.

The Dall-Miles system has experienced cable failure problems, which are believed to be caused by the sharp bends which the cables are forced to make as they exit the bridge of the clamp. Such failures result in the clamp loosening and tissue irritation caused by the frayed cable ends.

The Dall-Miles system is not particularly effective in providing rotational and vertical stability for the trochanter segment. Since the attachment cables must pass through the single bridge of the H-shaped clamp, the clamp can rotate about the bridge. Vertical stability is also lacking because the clamp is configured such that the cables must pass through the femur only in a single direction in the vicinity of the lesser trochanter.

Therefore, there is a perceived need for a device that can reliably reattach the greater trochanter to the femur following osteotomy, which provides maximum rotational and vertical stability, while minimizing the possibility of a failure resulting in loosening of the device or the necessity of its removal.

SUMMARY OF THE INVENTION

The present invention operates to stabilize and support the reattached greater trochanter section until it fuses to the femur. Rotational and vertical stability are provided. Proper healing is promoted by applying pressure evenly across the osteotomized surface.

A one-piece, bowl-shaped clamp is contoured to fit on the dome of the greater trochanter. The clamp is fixed and retained on the osteotomized trochanter section primarily through the use of surgical cables. Spikes project from the underside of the clamp to provide initial fixation and rotational stability and to prevent migration while union occurs at the osteotomy site.

In one embodiment, a central recess extends from the proximal to the distal aspect on the superior side of the clamp. Three pairs of cable grooves, designed to accommodate the cables used to anchor the clamp to the femur, intersect the central recess and extend along the full width of the clamp.

A swage is placed in the central recess in alignment with each pair of cable grooves for receiving the ends of a cable which is looped around the femur in various locations for holding the clamp in place. After the cables are tensioned, the swage is compressed to pinch the cables and hold them in place. The cable ends are trimmed to finalize the procedure.

In another embodiment of the present invention a series of spaced swages are formed integral with the clamp, each of which has a pair of openings for receiving the ends of a cable that fit in surface grooves or slots that extend across the face of the clamp.

BRIEF DESCRIPTION OF THE DRAWINGS

The objects, advantages and features of the invention will become more apparent when the detailed description of exemplary embodiments is considered conjunction with the appended drawings, in which:

FIG. 1 is a posterior view of the upper portion of the right femur indicating an osteotomy line for a cut at the base of the greater trochanter and removal of a section of the greater trochanter in such a manner that it may be reattached by means of the present invention;

FIG. 2 is a posterior view of the femur of FIG. 1, wherein the greater trochanter section has been removed and prepared for reattachment in accordance with the present invention;

DETAILED DESCRIPTION OF THE EXEMPLARY EMBODIMENTS

Referring to FIG. 1, reference letter F identifies a femur which has a greater trochanter T1 and a lesser trochanter T2. The femur F has been marked with an osteotomy cut line X in preparation for removal of a fragment or section W of the greater trochanter T1 in conjunction with hip surgery. Following removal of the section W and completion of the hip surgery, the section W is reattached by using a clamp 10 and surgical cables 50, 52 and 54 as described below.

In preparing the greater trochanter T1, a template (not shown) is overlaid on the outer surface of the greater trochanter T1 and a series of holes S are drilled. The osteotomy cut is then performed along an L-shaped cut line X and the resulting section W of the greater trochanter T1 is removed as shown in FIG. 1. An L-shaped osteotomy cut is preferred, since the resulting ledge L on the distal side provides greater rotational stability during healing. However, the clamp 10 can be used with any other osteotomy cut used to remove the greater trochanter.

As shown in FIG. 2, upon completion of the surgery where a prosthetic hip is implanted, the greater trochanter section W is repositioned on the femur F. A trochanter clamp 10 is positioned on greater trochanter section W, as shown, so that spikes 48 (FIG. 5), which project from the underside of the clamp 10, are aligned with holes S (FIG. 1). The section X with the clamp 10 in place is then repositioned on the superior lateral surface of the greater frochanter T1. Following a check for positioning and alignment of the clamp 10, cable holes about 2.0 mm. in diameter, designated by reference letters A, B, and C, are drilled through lesser trochant T2.

Figure 3:
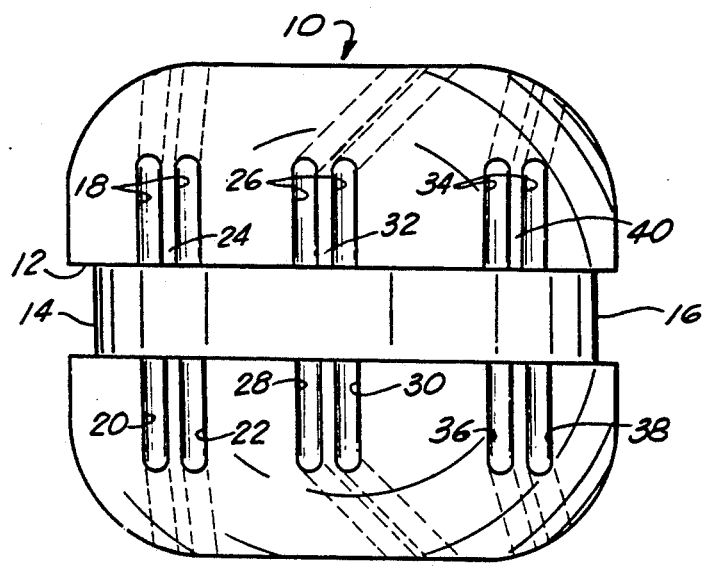
FIG. 3 is a top plan view of the upper surface of one embodiment of the clamp of the present invention.
Figure 4:
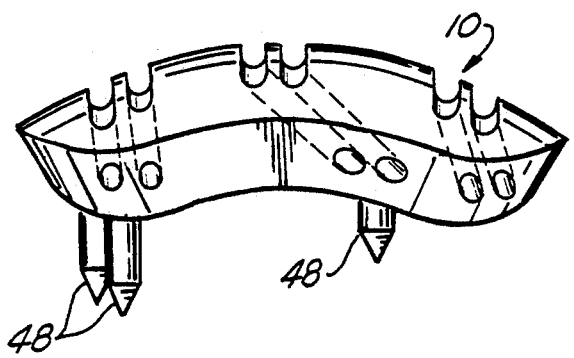
FIG. 4 is a side plan view of the trochanter clamp of FIG. 3.
Figure 5:
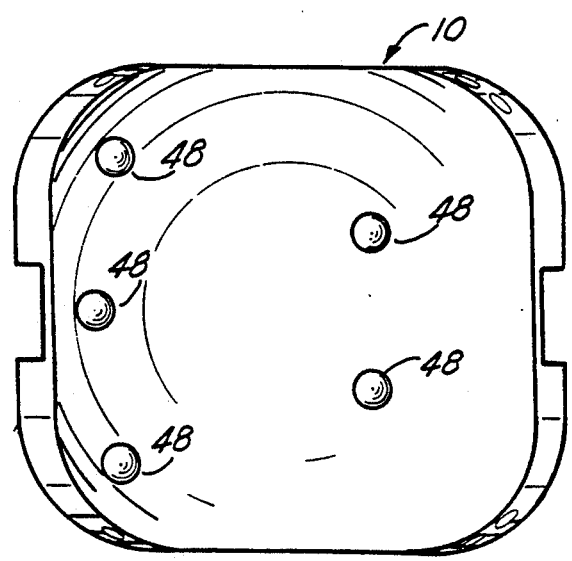
FIG. 5 is a plan view of the underside of the clamp of FIG. 3.

The clamp 10, as shown in detail in FIGS. 3-5, has an upper surface that is generally convex. A swage recess 12 is formed in the outer surface of the clamp 10 and extends longitudinally from a proximal side 14 to a distal side 16. Three pairs of cable grooves 18, 26 and 34 are formed in the outer surface of trochanter clamp 10, and extend in parallel alignment and generally perpendicular to the swage recess 12. The pairs of grooves 18, 26 and 34, are respectively identified by reference numerals 20 and 22, 28 and 30, and 36 and 38, with the grooves in each pair separated by ridges 24, 32 and 40, respectively.

The portions of the grooves adjacent to the recess 12 are open and deep enough to accommodate lengths of surgical cables as discussed below. At the outer edges of the clamp 10, the grooves conform to the contour of the clamp and are covered so they open on the sides of the clamp 10 as shown in FIG. 4.

The underside of the clamp 10 (FIG. 5) is generally concave in shape. A plurality of spikes 48, about 10-15 mm. long, project from the underside of clamp 10 and operate to initially align and hold the clamp 10 on the greater trochanter section W and on the greater trochanter T1 so the cables can be installed.

As shown in FIG. 2, a length of cable 50 is passed through the hole A with the ends located on both sides of the clamp 10 in close proximity to the grooves 20, 22. A second cable 52 is passed through the hole B, with its ends positioned on both sides of the clamp 10 in close proximity to the grooves 36, 38. Alternatively, the cable 52 could be looped around the base of the lesser trochanter T2 and hole B eliminated. A hole C is drilled through the lateral cortex of femur F at a distance of about 2.0 to 2.5 cm. from the distal side 16 of the clamp 10. A cable 54 is passed through the hole C so that its ends are positioned on both sides of the clamp 10 in close proximity to the grooves 28, 30.

The cables 50, 52 and 54 are about 1.6-2.0 mm. in diameter, with the holes A, B and C slightly larger. The cables are preferably formed of braided strands of chrome-cobalt wire. However, cables formed of wires of other metals that are biocompatible, as well as polymeric cables or polymer unifilaments, could also be used.

Figure 6:
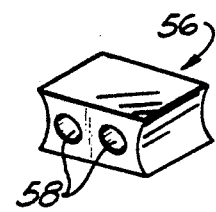
FIG. 6 is a perspective view of a swage designed for use with the clamp of FIGS. 1-4.

A swage 56 is provided for receiving the ends of each cable 50, 52 and 54 to hold them in place as described below. As shown in FIG. 6, the swages 56 are formed with a substantially rectangular cross-section, with a pair of parallel bores 58 to accommodate the cables 50, 52 or 54. The swages 56 have concave-shaped sides so that they are easily grasped by a suitable crimping tool (not shown).

Figure 7:
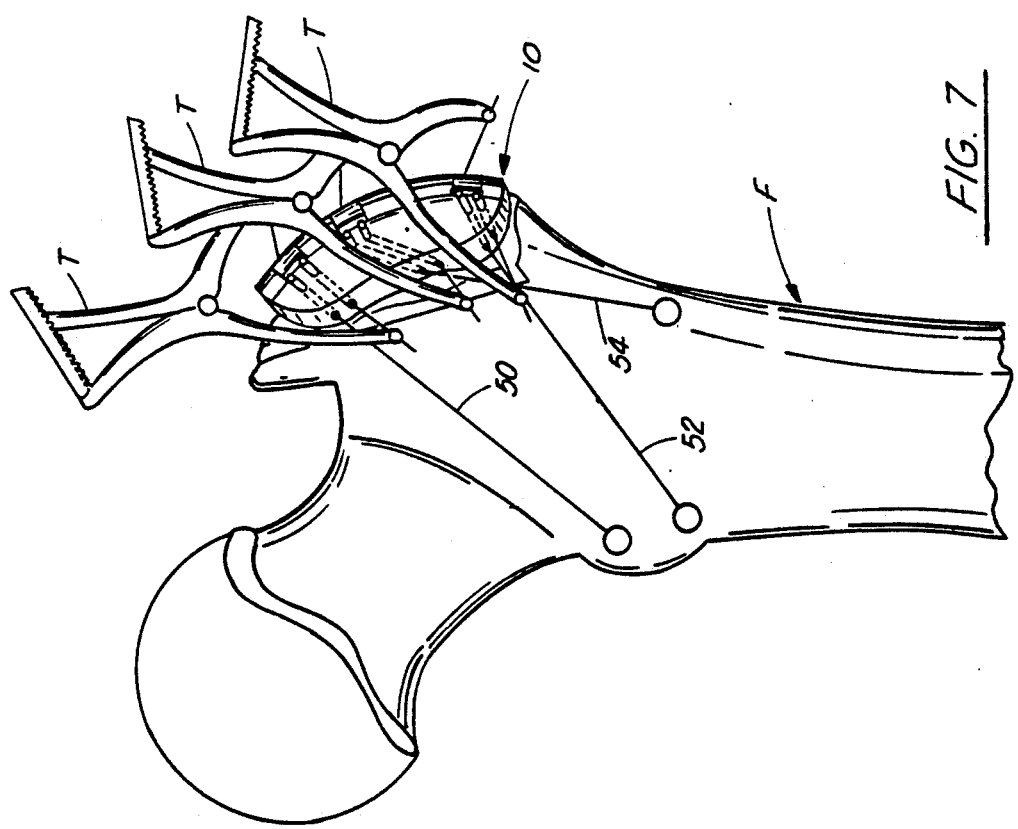
FIG. 7 is a posterior view of the femur of FIG. 2, wherein cable tensioners have been applied to tension the attachment cables.
Figure 9:
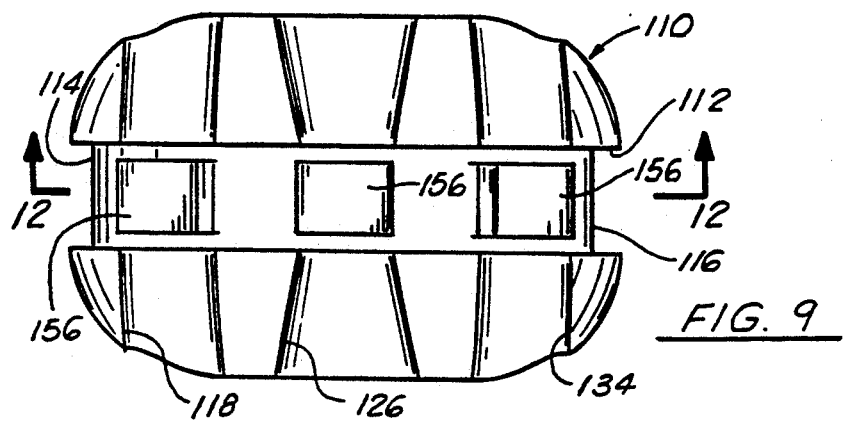
FIG. 9 is a plan view of the upper surface of a second embodiment of the trochanter clamp of the present invention.
Figure 12:
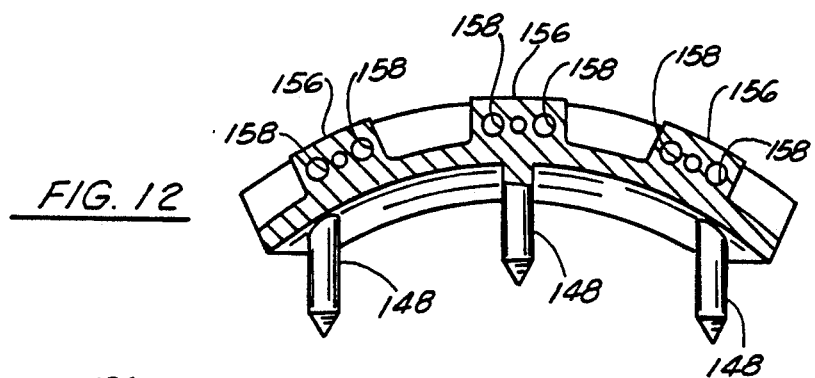
FIG. 12 is a sectional view of the clamp of FIG. 9, looking along the section line 12—12 in FIG. 9.
Figure 10:
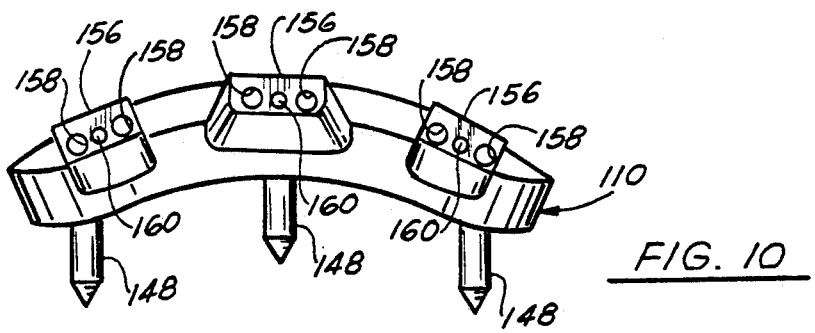
FIG. 10 is a side plan view of the clamp of FIG. 9.
Figure 11:
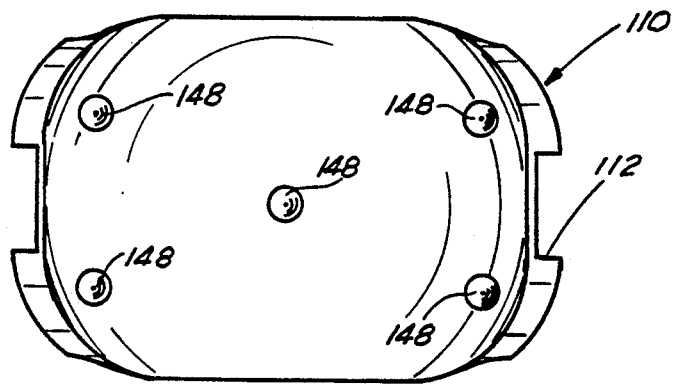
FIG. 11 is a bottom plan view of the clamp of FIG. 9.

As shown in FIG. 7, the swages 56 are inserted in the recess 12 so that the bores 58 are aligned with the adjacent cable grooves. The ends of the cables 50, 52 and 54 are inserted through the bores 58 and grasped by cable tensioners T. The cable tensioners T are used to apply tension to the cables 50, 52 and 54 until tension is evenly applied across the surface of clamp 10. The preferred tension in the wires 50, 52 and 54 generally ranges from about 125-200 pounds.

Figure 8:
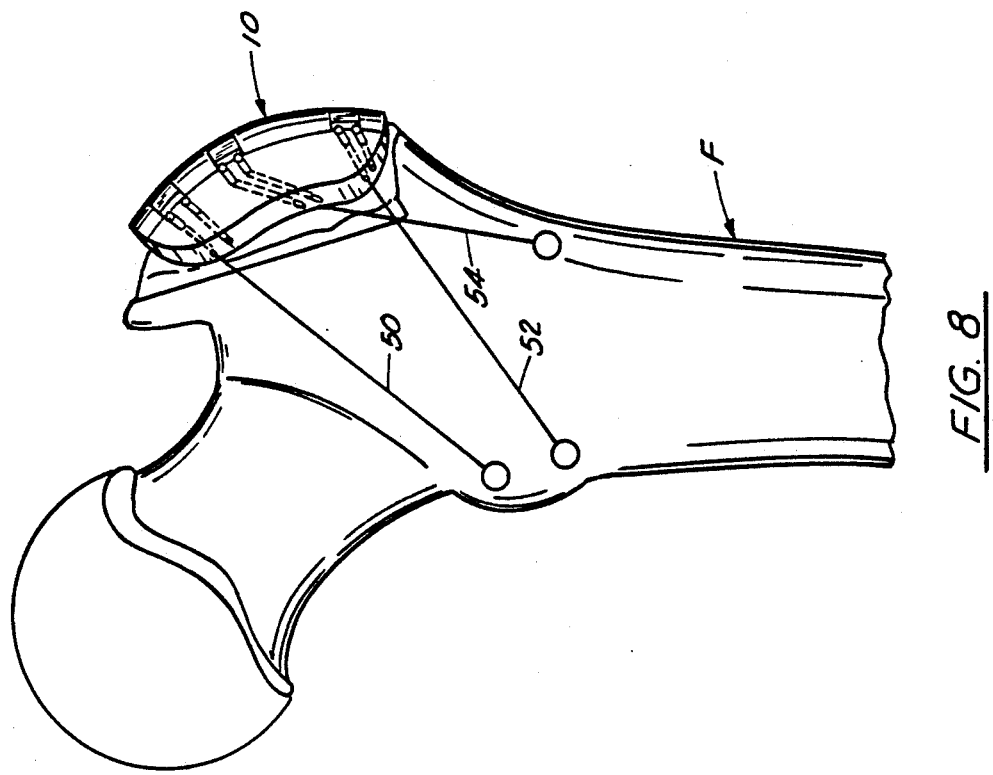
FIG. 8 is a posterior view of the femur of FIG. 2 following reattachment of the greater trochanter and illustrating the completed installation of the clamp and removed trochanter section.

Referring to FIG. 8, assembly of the cable system is completed by crimping the swages 56 with a suitable crimping tool (not shown) such that the bores 58 collapse to pinch the cables 50, 52 and 54 for maintaining them in tension. The recess 12 provides the necessary clearance for the crimping tool to grasp the swages 56. After the swages 56 are crimped, the tensioners T are released and removed. The ends of the wires 50, 52 and 54 are trimmed so that their ends lie within their respective grooves on the clamp 10. The trimming operation is preferably performed using a guillotine type cutter (not shown) to minimize the possibility of the cable ends fraying. The clamp could also be formed with countersunk holes (not shown) so that cancellous bone screws could be used as a supplemental connection to the underlying bone for additional initial stability.

FIGS. 9-12 show an alternative embodiment of the clamp, where a clamp 110 and swages 156 are formed as an integral piece. A swage recess 112 extends along the longitudinal access of the clamp 110, from its proximal side 114 to its distal side 116. The swages 156 are spaced along the recess 112, adjacent to grooves 118, 126 and 134 which are designed to accommodate the cables as discussed above in conjunction with the embodiment in FIGS. 1-8.

Each swage section 156 has a pair of cable holes 158 through which cables can be inserted from opposite directions discussed above. A center opening 160 is provided to allow the swages to collapse on the cables more uniformly when the swage sections 156 are crimped.

The grooves 118 and 134 are generally perpendicular to the recess 112 for receiving the cable 50 and 52, respectively, as shown in FIGS. 7 and 8. The groove 126 is flared at its outer ends to accommodate a cable such as the one illustrated with reference numeral 54 in FIGS. 7 and 8. The groove 126 is flared in both directions so that the clamp can be installed without concern about whether the ends are facing the right direction.

A plurality of spikes 148 project from the curved undersurface of the clamp 110 to engage holes drilled in the femur for providing greater lateral and rotational stability when the clamp is first installed. Installation of the cables for this embodiment is the same as described above, with the use of cable tensioners and crimping tools.

By using the clamps, along with the swages and cables described above, a greater trochanter or other bone section can be reattached after surgery and held firmly in place during the healing process. Rotating and shifting of the clamp and reattached bone section when the patient walks or raises out of a sitting position are resisted because the cables and clamp are positioned to counteract the forces acting on the clamp.

The foregoing disclosure and description of the invention are illustrative and explanatory thereof, and various changes in the size, shape and materials, as well as in the details of the illustrated construction may be made without departing from the spirit of the invention.

What is claimed is:

1. An implant for use in reattaching a bone section following bone surgery, comprising:
   (a) a plate-like member for fitting over at least a portion of the outer surface of the bone section to be reattached, the member having an inner surface for engaging the bone section and an outer surface facing away from the bone section and side walls extending between the inner and outer surface;
   (b) the outer surface having at least one cable holding portion for holding a cable in wherein said cable holding portion includes at least one groove place;
   (c) means, associated with the plate, for gripping the ends of a cable and holding the cable in tension on the cable holding portion; and
   (d) a recess extending across at least a portion of the outer surface of the plate-like member for receiving said means for gripping and holding, said recess intersecting the cable holding portion.

2. The implant of claim 1, wherein the outer surface is generally convex and the inner surface is generally concave.

3. The implant of claim 1, wherein the cable holding portion comprises three pairs of parallel grooves extending across the entire outer surface, and a wall separating each of the three pairs of parallel grooves, said wall having a height lower than the height of the outer surface of the plate-like member.

4. The implant of claim 3, wherein the three pairs of parallel grooves each have central portions opening onto the outer surface and end portions connecting with the central portion and extending through the plate-like member to openings in the side walls of the plate-like member.

5. The implant of claim 1, wherein the means for gripping and holding includes a generally rectangular body with opposing concave sides and a pair of openings parallel to the concave sides for receiving the ends of the cable, the body being collapsible by a crimping tool for pinching the cable in the openings.

6. The implant of claim 5, wherein the openings the rectangular body extend axially therethrough.

7. The implant of claim 1, wherein the means or gripping and holding is formed integral with the plate-like member.

8. The implant of claim 1, wherein the plate-like member further includes a plurality of spikes projecting from the inner surface of the plate for engaging the bone surface.

9. An implant for use in reattaching a bone section following bone surgery, comprising:
   (a) a plate-like member for fitting over at least a portion of the outer surface of the bone section to be reattached, the member having an inner surface for engaging the bone section and an outer surface facing away from the bone section;
   (b) the outer surface having at least one cable holding portion for holding a cable in place;
   (c) means, associated with the plate, for gripping the ends of a cable and holding the cable in tension on the cable holding portion, said means including a generally rectangular body with opposing concave sides and a pair of openings parallel to the concave sides for receiving ends of the cable, the body being collapsible by a crimping tool for pinching the cable in the openings.

10. The implant of claim 9, wherein the outer surface is generally convex and the inner surface is generally concave.

11. The implant of claim 9, wherein the cable holding portion comprises three pairs of parallel grooves extending across the entire outer surface, and a wall separating each of the three pairs of parallel grooves, said wall having a height lower than the height of the outer surface of the plate-like member.

12. The implant of claim 9, wherein the three pairs of parallel grooves each have central portions opening onto the outer surface and end portions connecting with the central portion and extending through the plate-like member to openings in the side walls of the plate-like member.

13. The implant of claim 9, wherein the openings in the rectangular body extends axially therethrough.

14. The implant of claim 9, wherein the plate-like member further includes a plurality of spikes projecting from the inner surface of the plate for engaging the bone surface.

15. A system for reattaching a removed bone section from the greater trochanter portion of a femur following hip surgery, comprising:
   (a) a plate-like member for fitting over at least a portion of the outer surface of the bone section to be reattached, the member having an inner surface for engaging the bone section and an outer surface facing away from the bone section;
   (b) the outer surface having a plurality of cable holding portions, said cable holding portions including pairs of grooves formed in the outer surface of the plate and extending laterally across the outer surface;
   (c) a plurality of cables, at least two of which is for extending around the femur and into two of the pairs of grooves, and another of said cables for extending around the distal side of the greater trochanter and into a third pair of grooves, one end of each cable being positioned on one of the grooves of each pair and the other end on the other groove of each pair;
   (d) means, associated with the plate, for gripping the ends of a cable and holding the cable in tension on the cable holding portion; and
   (e) a recess in the outer surface extending perpendicular to the grooves for receiving said means for gripping and holding.

16. The system of claim 15, wherein said means for gripping and holding includes a compressible swage to be received in the recess for receiving the ends of the cable in each groove, the swages being compressible for pinching the cables and holding them in tension.

17. The system of claim 15, wherein a plurality of spikes project outwardly from the inner surface of the plate-like member.

18. A system for reattaching a removed bone section from the greater trochanter portion of a femur following hip surgery, comprising:

(a) a plate-like member for fitting over at least a portion of the outer surface of the bone section to be reattached, the member having an inner surface for engaging the bone section and an outer surface facing away from the bone section;

(b) the outer surface having a plurality of cable holding portions, said cable holding portions including pairs of grooves formed in the outer surface of the plate and extending laterally across and opening onto a portion of the outer surface, the grooves extending through the member and having openings at the ends of the member;

(c) a plurality of cables, at least one of which is for extending around the femur and into two of the grooves, and an other of said cables for extending around the distal side of the greater trochanter and into a third groove;

(d) means, associated with the plate, for gripping the ends of a cable and holding the cable in tension on the cable holding portion; and (e) a recess, in the outer surface of the plate-like member, extending perpendicular to the grooves for receiving said means for gripping and holding, said recess intersecting each of the grooves.

19. The system of claim 18, wherein said means for gripping and holding includes a compressible swage to be received in the recess for receiving the ends of the cable in each groove, the swages being compressible for pinching the cables and holding them in tension.

20. The system of claim 18, wherein a plurality of spikes project outwardly from the inner surface of the plate-like member.

21. A method for reattaching a removed bone section, comprising the steps of:

(a) positioning a plate-like member on the outer surface of the removed section, the plate-like member having removable cable gripping and holding means on the outer surface;

(b) forming at least one hole in the bone on the opposite side of the removed bone section;

(c) wrapping at least one length of cable around the bone and through the opening, with both ends being passed through opposite sides of the cable gripping and holding means;

(d) tensioning the cable by pulling on the ends; and (e) securing the cable gripping and holding means on the cable ends for holding the cable in tension.

22. The method of claim 21, and further including the steps of:

forming locating holes in the outer surface of a greater trochanter portion of a femur, which are aligned with spikes formed on the undersurface of the plate-like member;

removing a section off the greater trochanter, the holes extending into the bone beneath the removed section; and inserting the spikes on the undersurface of the plate-like member into the holes when the plate-like member is positioned on the removed section of the greater trochanter.

23. The method of claim 22, and further including the step of:

forming two holes in the lesser trochanter spaced from each other and a third hole through the lateral cortex of the femur.

24. The method of claim 23, and further including the step of:

placing a plurality of compressible swages, one for each cable in a recess formed in the outer surface of the plate-like member; with openings in the swages adapted to receive the ends of the cables;

passing the cables over grooves formed in the outer surface of the plate-like member, one set for such cable, the grooves intersecting with the recesses, and into the openings in the swages; and compressing the swages to secure the swages on to cables.

25. The method of claim 24, wherein the grooves are spaced from the proximal to the distal sides of the plate-like member, the cables in the proximal and distal sides being passed through the holes formed in the lesser trochanter, while the cable in the other groove being passed through the hole in the lateral cortex.

26. The method of claim 23, wherein the step of removing a section off of the greater trochanter includes making an L-shaped cut to form a ledge on the distal side of the cut.

27. The method of claim 23, and further including the steps of:

passing a first cable through one of the holes in the lesser trochanter and over one of the grooves;

passing a second cable through the second hole in the lesser trochanter and over a second grooves;

passing a third cable through the hole in the lateral cortex of the femur and over a third groove; and tensioning the cables over the member.

* * * * *